United States Patent
Harding

(10) Patent No.: US 9,222,898 B2
(45) Date of Patent: Dec. 29, 2015

(54) X-RAY DIFFRACTION IMAGING SYSTEM WITH INTEGRATED SUPERMIRROR

(71) Applicant: Morpho Detection, LLC, Newark, CA (US)

(72) Inventor: Geoffrey Harding, Hamburg (DE)

(73) Assignee: MORPHO DETECTION, LLC, Newark, CA (US)

( * ) Notice: Subject to any disclaimer, the term of this patent is extended or adjusted under 35 U.S.C. 154(b) by 126 days.

(21) Appl. No.: 14/228,948

(22) Filed: Mar. 28, 2014

(65) Prior Publication Data
US 2015/0276628 A1 Oct. 1, 2015

(51) Int. Cl.
*G01N 23/20* (2006.01)
*G21K 1/02* (2006.01)

(52) U.S. Cl.
CPC ............ *G01N 23/20008* (2013.01); *G21K 1/02* (2013.01); *G21K 2201/067* (2013.01)

(58) Field of Classification Search
CPC ............... G01N 23/207; G01N 23/20; G01N 23/20008; G01N 23/2076; G01N 2223/316; G01V 5/0025; G21K 1/025
See application file for complete search history.

(56) References Cited

U.S. PATENT DOCUMENTS

| 5,082,621 | A | 1/1992 | Wood | |
|---|---|---|---|---|
| 5,167,912 | A | 12/1992 | Wood | |
| 7,635,839 | B2 | 12/2009 | Cho et al. | |
| 7,756,249 | B1 | 7/2010 | Harding | |
| 7,787,591 | B2 * | 8/2010 | Harding | G01V 5/00 378/149 |
| 7,835,495 | B2 | 11/2010 | Harding | |
| 8,537,970 | B2 | 9/2013 | Bernhardt | |
| 2007/0030947 | A1 * | 2/2007 | Popescu | A61B 6/022 378/19 |
| 2007/0133749 | A1 * | 6/2007 | Mazin | G21K 1/025 378/147 |
| 2012/0263275 | A1 | 10/2012 | Harding et al. | |

OTHER PUBLICATIONS

Extended European Search Report, dated Aug. 3, 2015, for co-pending EP patent application No. EP15000797.9 (5 pgs.).

* cited by examiner

*Primary Examiner* — Hoon Song
(74) *Attorney, Agent, or Firm* — Armstrong Teasdale LLP

(57) ABSTRACT

An x-ray diffraction imaging (XDI) system includes a plurality of x-ray sources configured to generate x-rays directed toward an object. The XDI system also includes a primary collimator positioned a distance from the plurality of x-ray sources. A plurality of nodes are defined within the primary collimator at a plurality of node distances from the plurality of x-ray sources. Each node of the plurality of nodes defines an x-ray intersection region. The XDI system further includes a supermirror assembly including a plurality of mounting rails positioned adjacent the plurality of nodes.

20 Claims, 5 Drawing Sheets

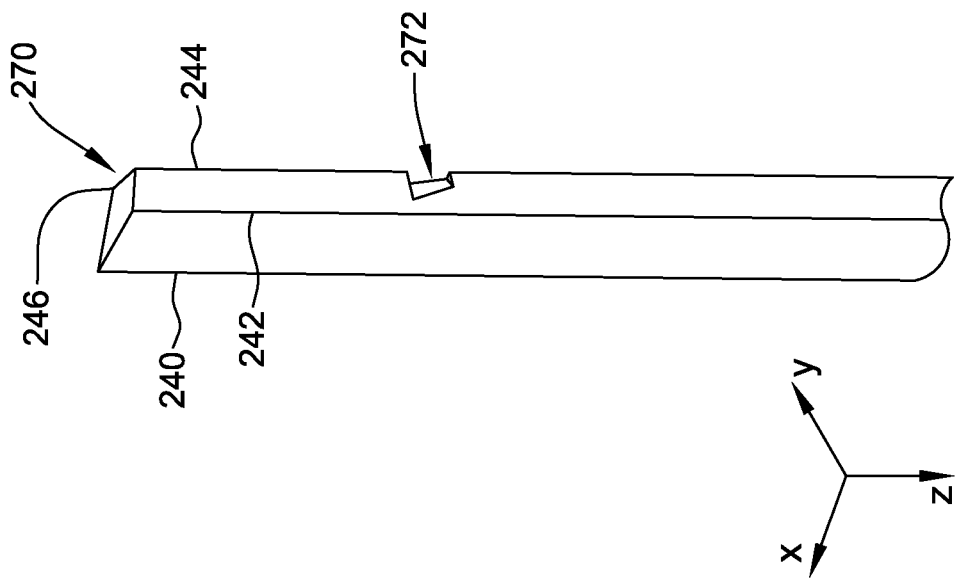
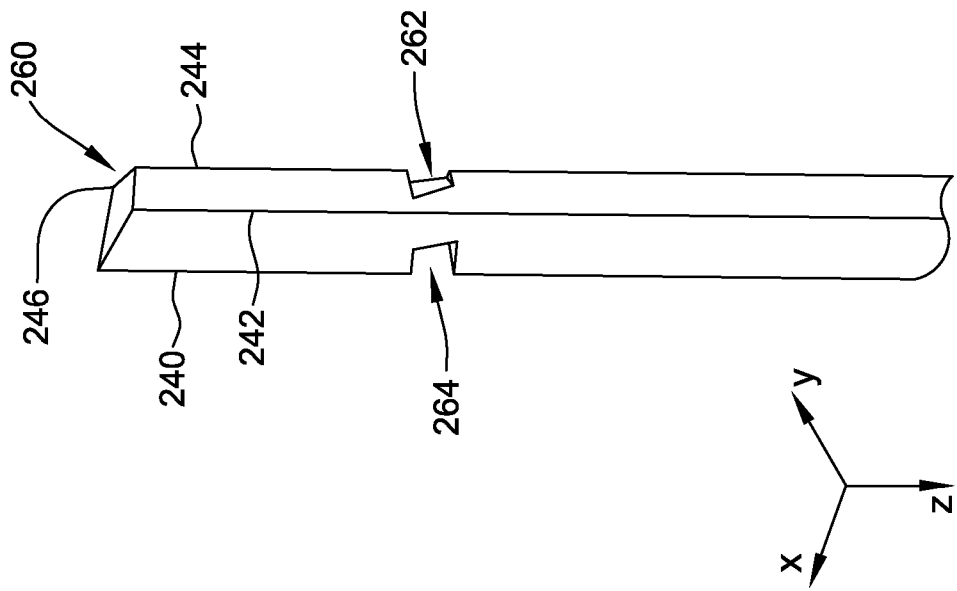
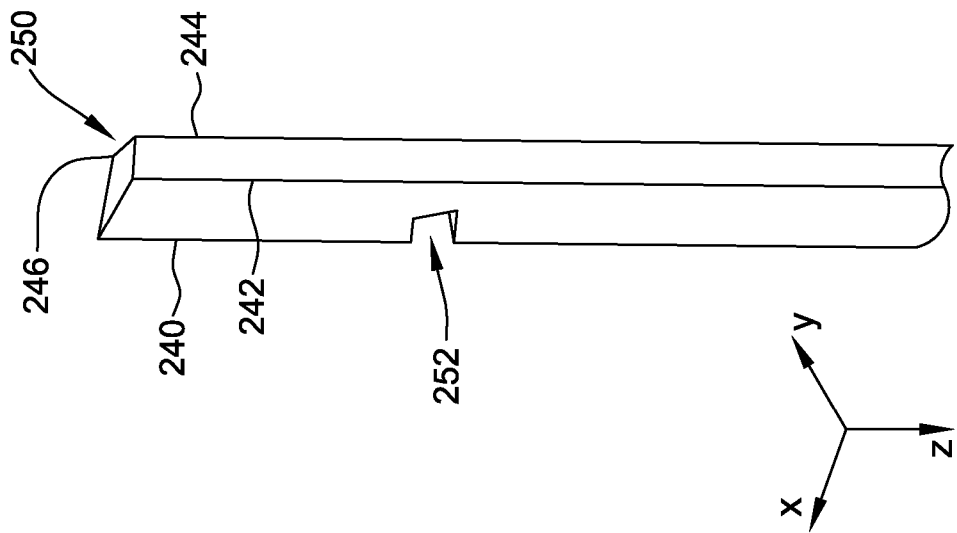

X-RAY DIFFRACTION IMAGING SYSTEM WITH INTEGRATED SUPERMIRROR

BACKGROUND OF THE INVENTION

The embodiments described herein relate generally to an x-ray diffraction imaging (XDI) system and, more particularly, to an XDI system with an integrated supermirror.

Known security detection systems are used at travel checkpoints to inspect carry-on and/or checked bags for concealed weapons, narcotics, and/or explosives. At least some known security detection systems include x-ray imaging systems. In an x-ray imaging system, an x-ray source transmits x-rays through an object or a container, such as a suitcase, towards a detector, and the detector output is processed to identify one or more objects and/or one or more materials in the container.

At least some known security detection systems include an XDI system, e.g., a multi-detector inverse fan beam (MIFB) XDI system that uses an inverse fan-beam geometry (a large source and a small detector) and a multi-focus x-ray source (MFXS). At least some known XDI systems provide an improved discrimination of materials, as compared to that provided by other known x-ray imaging systems, by measuring d-spacings between lattice planes of micro-crystals in materials. Further, x-ray diffraction may yield data from a molecular interference function that may be used to identify other materials, such as liquids, in a container.

Known MIFB XDI systems feature an x-ray multisource emitting a multiplicity of x-ray beams, such that each object voxel is irradiated from several different directions, and such that these systems measure spatially-resolved x-ray diffraction profiles of the constituent voxels of inhomogeneous, extended objects. An important requirement of x-ray screening, whether for solid-state, liquid, amorphous or other types of explosives, is to enhance the detection performance while reducing the false alarm rate. MIFB XDI systems have an intrinsically excellent detection performance when the number of detected scatter photons is large. However, to attain the necessary x-ray flux, such systems typically require high electric power draws for the associated high-powered x-ray sources, and this electric power must be provided at the location where the XDI screener is operated. This because the x-rays are generated by point x-ray sources and these x-rays are subject to divergent emission.

The use of mirrors to reflect x-rays that otherwise would be lost due to normal fanning of x-rays has been considered. The mirrors would facilitate increasing the x-ray flux by directing the fanning x-rays into a parallel x-ray beam, thereby decreasing the requirements for high electric power draws. The use of supermirrors to reflect even a greater number of x-rays in a coherent manner facilitates further reductions in the power draw. Known supermirrors are depth-graded multi-layer mirrors that include a layer of glass upon which is formed a plurality of alternating layers of high-density and low-density material, such as tungsten and silicon. These supermirrors have a mirrored face directed towards the x-rays and an uncoated face on the side opposite the x-rays. Such supermirrors are typically used in x-ray telescopes to enhance the x-ray flux collected for astronomical observations. However, known configurations for such supermirrors include a framing system that holds the mirrors "face-on" at the uncoated face. As such, these known configurations of the supermirrors are incompatible with many known XDI MIFB topologies that include a plurality of planes of x-rays extracted from the same x-ray sources without adding additional sources. As such, the adjacent x-ray planes are too close to each other to allow a face-on mirror frame structure.

BRIEF DESCRIPTION OF THE INVENTION

In one aspect, an x-ray diffraction imaging (XDI) system is provided. The XDI system includes a plurality of x-ray sources configured to generate x-rays directed toward an object. The XDI system also includes a primary collimator positioned a distance from the plurality of x-ray sources. A plurality of nodes are defined within the primary collimator at a plurality of node distances from the plurality of x-ray sources. Each node of the plurality of nodes defines an x-ray intersection region. The XDI system further includes a supermirror assembly including a plurality of mounting rails positioned adjacent the plurality of nodes.

In another aspect, a supermirror assembly for an x-ray diffraction imaging (XDI) system is provided. The XDI system includes a plurality of x-ray sources and a primary collimator positioned a distance from the plurality of x-ray sources. A plurality of nodes is defined within the primary collimator at a plurality of node distances from the plurality of x-ray sources. Each node of the plurality of nodes defines an x-ray intersection region. The supermirror assembly includes a plurality of mounting rails positioned adjacent the plurality of nodes.

BRIEF DESCRIPTION OF THE DRAWINGS

FIGS. 1-7 show exemplary embodiments of the systems and methods described herein.

FIG. 1 is a schematic view of an exemplary x-ray diffraction imaging (XDI) system in an X-Y plane;

FIG. 2 is a schematic view of a magnified portion of the XDI system shown in FIG. 1 taken at area 2 with an exemplary supermirror assembly;

FIG. 3 is a schematic view of the supermirror assembly shown in FIG. 2 in an X-Z plane and taken along line 3-3 shown in FIG. 2;

FIG. 4 is a schematic view of a first exemplary mounting rail that may be used with the supermirror assembly shown in FIG. 3;

FIG. 5 is a schematic view of a second exemplary mounting rail that may be used with the supermirror assembly shown in FIG. 3;

FIG. 6 is a schematic view of a third exemplary mounting rail that may be used with the supermirror assembly shown in FIG. 3; and FIG. 7 is a schematic cross-sectional view of a supermirror segment that may be used with supermirror assembly shown in FIG. 2.

DETAILED DESCRIPTION OF THE INVENTION

The multi-detector inverse fan beam (MIFB) x-ray diffraction imaging (XDI) systems described herein facilitate a cost-effective integration of a supermirror within the MIFB XDI system. The supermirrors described herein reflect x-rays to reduce the number of x-rays lost due to standard divergent flux spreading, i.e., x-ray fanning. Specifically, the supermirrors described herein facilitate integration of x-ray supermirrors in an XDI primary collimator to enhance x-ray flux while reducing power draws. Also, the supermirrors described herein include mounting rails that facilitate mounting the supermirrors in the XDI systems to be compatible with conventional MIFB XDI topologies with an "edge-on" mirror-edge-in-rail-slot configuration rather than the known "face-on" framing configuration. As such, the supermirrors described herein facilitate multiple planes of x-ray fan beams from a single array of point x-ray sources. In addition, since the mounting rails are positioned in regions that have little x-ray flux values, there is substantially no loss of x-ray radiation through supermirror frame holders that would otherwise obscure useful x-rays. Furthermore, the mirror support rails are manufactured from strong, but lightweight and inexpensive materials, thereby decreasing the weight and cost of the MIFB XDI systems described herein.

Figure 1:
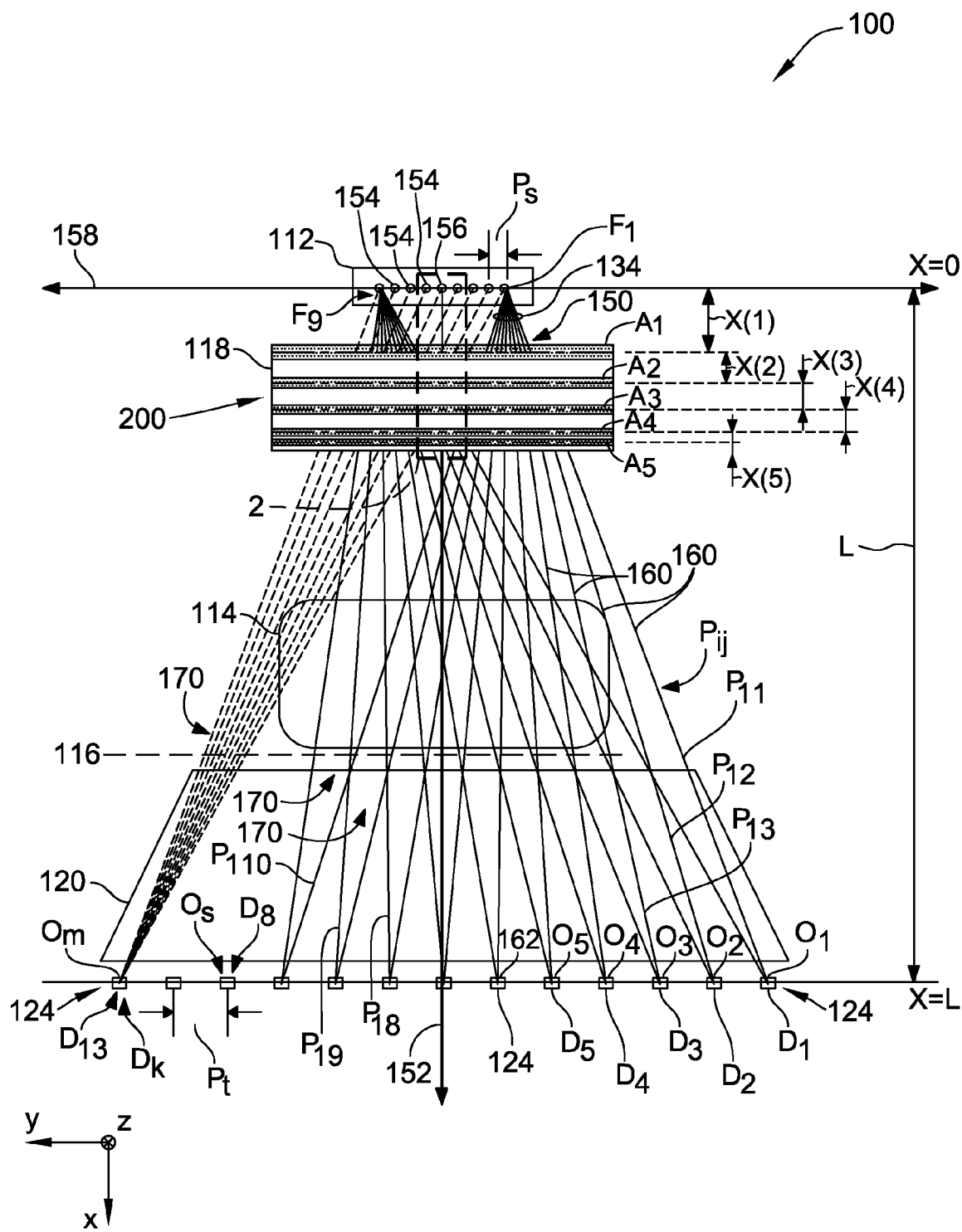

FIG. 1 is a schematic view of an exemplary x-ray diffraction imaging (XDI) system 100 in an X-Y plane. In the exemplary embodiment, XDI system 100 is a multi-detector inverse fan beam x-ray diffraction imaging (MIFB XDI) system. Alternatively, system 100 is any XDI system that enables operation of system 100 as described herein. XDI system 100 includes a multi-focus x-ray source (MFXS) 112, an examination area 114, a support 116 configured to support an object, a primary collimator 118, and a secondary collimator 120. XDI system 100 also includes two types of detectors, an array of transmission detectors (not shown) and a plurality of discrete coherent x-ray scatter detectors 124. The transmission detectors are offset in a z-axis direction from coherent x-ray scatter detectors 124.

In the exemplary embodiment, MFXS 112 is capable of emitting x-ray radiation sequentially from a plurality of focus points, as described below, distributed along MFXS 112 in a direction substantially parallel to a y-axis perpendicular to the z-axis. In the exemplary embodiment, MFXS 112 has nine (9) focus points. In alternative embodiments, MFXS 112 has approximately 40 to 100 focus points. Also alternatively, MFXS 112 may include any suitable number of focus points that enables operation of XDI system 100 as described herein.

Further, in the exemplary embodiment, MFXS 112 is located on or coupled to an upper support surface, such as at or near a ceiling, while the transmission detectors and coherent x-ray scatter detectors 124 are located on, or coupled to, a lower support structure, such as at or near a floor. In an alternative embodiment, MFXS 112 is located on or coupled to a lower support structure, such as at or near a floor, while the transmission detectors and coherent x-ray scatter detectors 124 are located on or coupled to an upper support surface, such as at or near a ceiling. Further, in the exemplary embodiment, MFXS 112, the transmission detectors and coherent x-ray scatter detectors 124 are stationary, support 116 is a conveyor belt capable of movement backward and forward in a direction substantially parallel to the z-axis, and examination area 114 is a baggage tunnel through which the conveyor belt moves. In an alternative embodiment, MFXS 112, the transmission detectors and coherent x-ray scatter detectors 124 are capable of coordinated movement at least in a direction substantially parallel to the z-axis, and support 116 is stationary. In certain alternative embodiments, MFXS 112, the transmission detectors, coherent x-ray scatter detectors 124, and support 116 are all capable of movement.

In the exemplary embodiment, MFXS 112 is configured to emit, through primary collimator 118, a set of x-ray pencil beams 134, from each focus point of MFXS 112. A portion of the x-ray radiation from each pencil beam 134 typically is scattered in various directions upon contact with a container (not shown) in examination area 114. Secondary collimator 120 is configured to facilitate ensuring that a portion of scattered radiation (not shown) arriving at each coherent x-ray scatter detector 124 has a constant scatter angle with respect to the corresponding pencil beam 134 from which the scattered radiation originated.

In the exemplary embodiment, a multi-detector inverse fan beam 150 formed from a set of x-ray pencil beams 134 is projected along x-axis 152 onto the X-Y plane. More specifically, pencil beams 134 of fan beam 150 fan out in the X-Y plane. Pencil beams 134 of fan beam 150 also fan out in the X-Z plane. In one embodiment, MFXS 112 emits radiation sequentially from a plurality of focus points 154. More specifically, MFXS 112 includes an anode 156 and a plurality of focus points 154 arranged along a length of anode 156 colinear with a y-axis 158 of MFXS 112. Each focus point 154 is sequentially activated to emit an x-ray fan beam. For example, a focus point $F_1$ emits fan beam MIFB 150 that extends between and is detected by coherent x-ray scatter detector $D_1$ through and including coherent x-ray scatter detector $D_{13}$ and includes a plurality of pencil primary beams 160. Focus points 154 are denoted $F_1, F_2, \ldots F_i, \ldots F_n$ with a running index i. Primary collimator 118 is configured to select from the radiation emitted at each focus point 154, primary beams that are directed to a series of convergence points 162 labeled $O_1, O_2, \ldots, O_j, \ldots O_m$ with a running index j regardless of which focus point 154 is activated. Ten primary beams 160 are shown in FIG. 1 with each primary beam 160 emitted from focus point $F_1$ directed to a corresponding convergence point $O_1, O_2, \ldots, O_j, \ldots O_{10}$ positioned along a line parallel to y-axis 158 at a coordinate X=L with focus point $F_1$ activated.

A plurality of discrete coherent x-ray scatter detectors 124 labeled discrete coherent x-ray scatter detectors $D_1, D_2, \ldots D_j, \ldots D_k$ with a running index j are positioned at a suitable or desirable distance in a direction along the Z-axis from a corresponding convergence point 162 to record coherent scatter from primary beam $P_{ij}$ in discrete coherent x-ray scatter detector $D_j$. A combination of MFXS 112 and discrete coherent x-ray scatter detectors 124 facilitates examining a volume of an object positioned within examination area 114 without any dead area from which no XDI signal is detected or measured.

As primary beam 160 labeled $P_{ij}$ propagates through an object (not shown) positioned within examination area 114, primary beam $P_{ij}$ interacts with the object to produce coherent scatter that may be detected in coherent x-ray scatter detectors $D_{j+1}, D_{j+2}, D_{j-1}$, and/or $D_{j-2}$, for example. Primary beams $P_{11}, P_{12}, P_{13}, P_{14}, P_{15}, \ldots P_{1m}$ are emitted from focus point $F_1$ and directed to corresponding convergence points $O_1, O_2, O_3, O_4, O_5, \ldots O_m$, respectively. As each primary beam $P_{11}, P_{12}, P_{13}, P_{14}, P_{15}, \ldots P_{1m}$ moves through examination area 114, each primary beam $P_{11}, P_{12}, P_{13}, P_{14}, P_{15}, \ldots P_{1m}$ collides with and/or interacts with an object (not shown) positioned within examination area 114 to produce coherent scatter (not shown) that is detectable at one or more coherent x-ray scatter detectors $D_1, D_2, D_3, D_4, D_5, \ldots D_k$, for example.

In the exemplary embodiment, MFXS 112 is positioned on the y-axis (x=0) of a Cartesian coordinate system. Each focus point 154 has a position on a grid having a pitch, $P_s$. Further, convergence points 162 lie parallel to the y-axis at coordinate X=L, and each convergence point 162 has a position on a grid having a pitch, $P_t$. In a particular embodiment, for an XDI checked baggage screening system, L has a value of about 2000 millimeters (mm), $P_s$ has a value of about 20 mm, and $P_t$ has a value of about 200 mm. Alternatively, L, $P_s$, and $P_t$ have any values that enable operation of XDI system 100 as described herein.

A plurality of coherent x-ray scatter detectors 124 are positioned at the same y-coordinate as convergence points 162. One pair of coherent x-ray scatter detectors 124 may be associated with a corresponding convergence point 162 with the pair of coherent x-ray scatter detectors 124 positioned on both sides of the X-Y plane. In a further embodiment, thirteen (13) convergence points are used to allow for several convergence point position arrangements to incorporate a different number of coherent x-ray scatter detectors 124. If all convergence points 162 have detector pairs then XDI system 100 may include twenty-six (26) coherent x-ray scatter detectors 124. In alternative embodiments, fewer coherent x-ray scatter detectors 124 may be positioned at convergence point positions 1, 3, 5, 7, 9, 11, and 13, at convergence point positions 1, 4, 7, 10, and 13, or at convergence point positions 1, 5, 9, and 13 to account for manufacturing and/or cost constraints. An MIFB configuration including 13 convergence points spanning a width in the Y direction in total of 2000 mm requires a fan angle from each focus point 54 of about 55° in the y-axis direction.

A left-most detector $D_{13}$ detects a plurality of primary beams 60 labeled $P_{113}$, $P_{213}$, ... $P_{ij}$, ... $P_{913}$, alternatively referred to herein as an inverse fan beam bundle 170 of primary beams, from each focus point 154 denoted $F_1$, $F_2$, ... $F_i$, ... $F_9$ of MFXS 112 that are transmitted by primary collimator 118. Inverse fan beam bundle 170 is significantly narrower than a width of examination area 114. MFXS 112, as depicted in FIG. 1 is not shown to scale for clarity's sake, and may be smaller than shown. Moreover, only 13 convergence points 162 are shown although, as described above, in practice the number of convergence points 162 can be much greater. Further, the scatter signal is proportional to a number of coherent x-ray scatter detectors 124 incorporated into XDI system 100.

Several inverse fan beam bundles 170 of primary beams directed towards a corresponding convergence point $O_j$ are detected by a corresponding coherent x-ray scatter detector $D_j$. During a scan of the object positioned within examination area 114, during which each focus point 154 of MFXS 112 is sequentially activated, the object section is completely irradiated and scatter signals are measured from an entire width of the object. In this embodiment, no mechanical movements are required to achieve a complete 2-D scan of the object. MFXS 112 achieves this with only a small x-ray source dimension along the y-axis. In the exemplary embodiment, MFXS 112 has a length along the y-axis of less than about 500 mm. A small x-ray source dimension is advantageous from the viewpoints of cost and reliability.

Also, in the exemplary embodiment, a supermirror assembly 200 is positioned within primary collimator 118. As will be described further below, a plurality of nodes (not shown in FIG. 1) are defined within primary collimator 118, where the nodes are defined regions of x-ray intersection within primary collimator 118. The nodes define node arrays $A_1$, $A_2$, $A_3$, $A_4$, and $A_5$ that are parallel to y-axis 158 and the X-Y plane. Node array $A_1$ is positioned a predetermined node distance $X(1)$ from MFXS 112. Also, node array $A_2$ is positioned a predetermined distance $X(2)$ from node array $A_1$. Further, node array $A_3$ is positioned a predetermined distance $X(3)$ from node array $A_2$. Moreover, node array $A_4$ is positioned a predetermined distance $X(4)$ from node array $A_3$. In addition, node array $A_5$ is positioned a predetermined distance $X(5)$ from node array $A_4$. In general, node array $A_N$ is positioned a predetermined distance $X(N)$ from node array $A_{N-1}$.

Predetermined node distances $X(1)$ through $X(5)$ are calculated from the expression:

$$X(N) = L/[1+(N*P_t)/P_s], \text{ where} \qquad \text{Eq. 1}$$

$X(N)$ is the predetermined node distance, N is an integer, L is the length between MFXS 112 and coherent x-ray scatter detectors 124 along the x-axis 152 as described above, $P_t$ is the detector pitch as described above, and $P_s$ is the source pitch as described above. There are N node arrays, i.e., in the exemplary embodiment, there are five node arrays. Node array $A_1$ includes a plurality of first order nodes, node array $A_2$ includes a plurality of second order nodes, node array $A_3$ includes a plurality of third order nodes, node array $A_4$ includes a plurality of fourth order nodes, and node array $A_5$ includes a plurality of fifth order nodes.

In the exemplary embodiment, L has a value of about 2000 millimeters (mm), $P_s$ has a value of about 20 mm, and $P_t$ has a value of about 200 mm. Alternatively, L, $P_s$, and $P_t$ have any values that enable operation of XDI system 100 as described herein. Therefore, predetermined node distance $X(1)$ is approximately 181.8 mm, predetermined node distance $X(2)$ is approximately 95.2 mm, predetermined node distance $X(3)$ is approximately 64.5 mm, predetermined node distance $X(4)$ is approximately 48.8 mm, and predetermined node distance $X(5)$ is approximately 39.2 mm.

Figure 2:
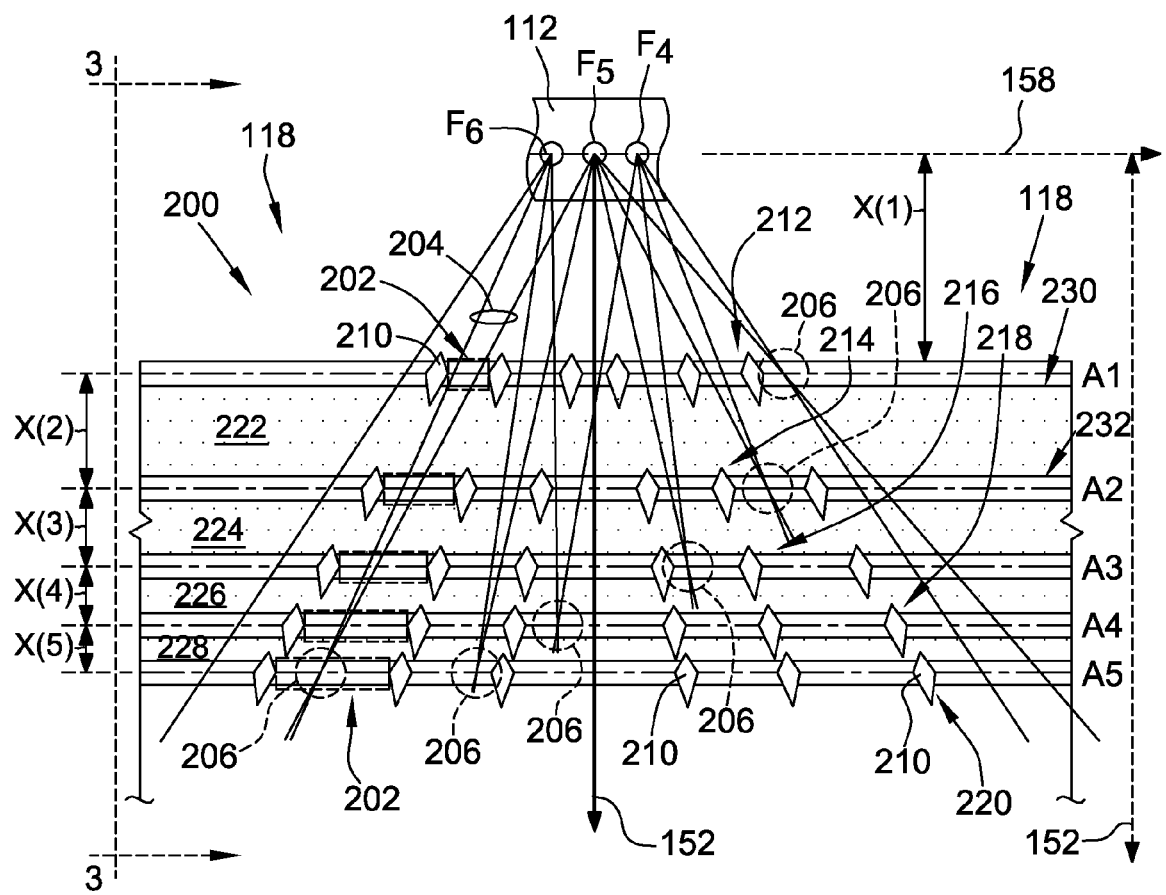

FIG. 2 is a schematic view of a magnified portion of XDI system 100 (shown in FIG. 1) taken at area 2 (shown in FIG. 1). Each of node arrays $A_1$ through $A_5$ and each of node distances $X(1)$ through $X(5)$ are shown. Each node array $A_N$ includes a plurality of nodes 202 defined within primary collimator 118, where nodes 202 are defined by regions of x-ray intersection within primary collimator 118. For example, five successive nodes 202 are shown and a pair of x-rays 204 are shown traveling through one of nodes 202 at intersection point 206 as circled. Additional nodes 202 are shown (but not labeled) and a plurality of intersection points are shown. For purposes of clarity, not all of nodes 202 are labeled and additional intersecting x-rays within each node 202 are not shown. The only x-rays that propagate through XDI system 100 are those x-rays that include the bundles of rays that intersect at nodes 202. In contrast to nodes 202, the spaces adjacent (to the left or right) of each node 202 are substantially devoid of radiation.

Supermirror assembly 200 includes a plurality of mounting rails 210 positioned proximate each of nodes 202, thereby reducing the potential for blocking useful radiation. Mounting rails 210 extend perpendicular to the X-Y plane along the Z-axis and node arrays $A_1$ through $A_5$ are substantially parallel to the X-Y plane and substantially parallel to each other. Therefore mounting rails 210 are substantially perpendicular to node arrays $A_1$ through $A_5$. In the exemplary embodiment, mounting rails 210 are trapezoidal in shape and are approximately 100 mm in length. Alternatively, mounting rails 210 have any shape and any length that that enables operation of XDI system 100 as described herein. Mounting rails 210 form a plurality of mounting rail arrays 212, 214, 216, 218, and 220 that intersect node arrays $A_1$ through $A_5$, respectively.

Also, in the exemplary embodiment, supermirror assembly 200 includes a plurality of mirrored segments, i.e., four segments 222, 224, 226, and 228. Alternatively, any number of mirrored segments that enables operation of supermirror assembly 200 as described herein is used. Mirrored segment 222 extents between node arrays $A_1$ and $A_2$, mirrored segment 224 extents between node arrays $A_2$ and $A_3$, mirrored segment 226 extents between node arrays $A_3$ and $A_4$, and mirrored segment 228 extents between node arrays $A_4$ and $A_5$. Each of mirrored segments 222 through 228 includes a first edge 230 that is received within a first set of grooves (not shown in FIG. 2, and discussed further below) formed in a first set of mounting rails 210. Each of mirrored arrays 220 also includes a second edge 232 that is received within a second set of grooves (not shown in FIG. 2, and discussed further below) formed in a second set of mounting rails 210. For example, each mounting rail 210 associated with mounting rail array 212 includes a first groove and each mounting rail 210 associated with mounting rail array 214 includes a second groove. First edge 230 is slid through the first grooves and second edge 232 is slid through the second grooves. Mirrored segment 222 forms a friction fit with mounting rail arrays 212 and 214. Alternatively, any coupling mechanism that enables operation of supermirror assembly 200 as described herein is used, including, without limitation, mounting shims and adhesives. Similar configurations are used for mirrored segments 224, 226, and 228 with respective adjacent mounting rails arrays 214, 216, 218, and 220, respectively.

Figure 3:
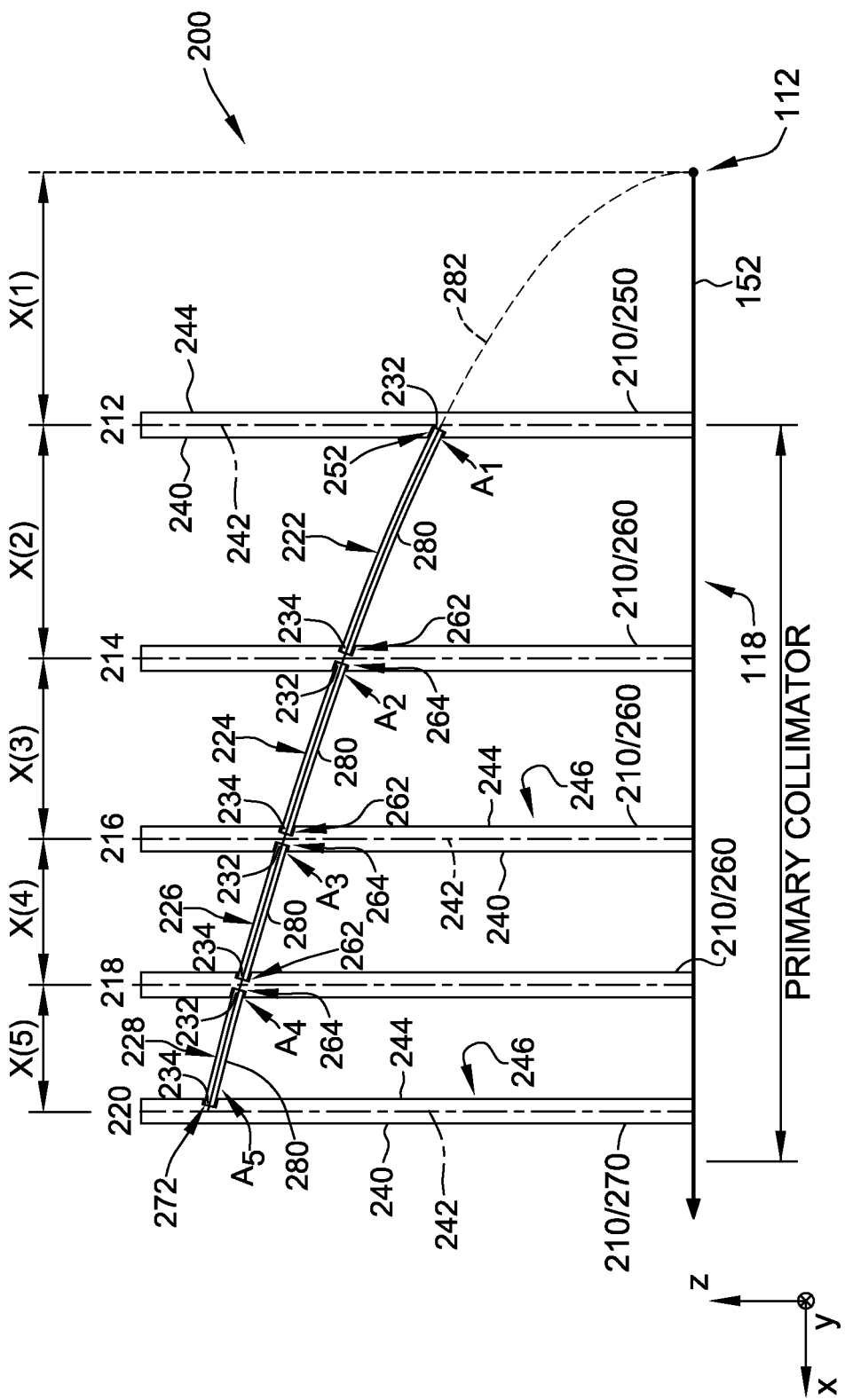

FIG. 3 is a schematic view of supermirror assembly 200 in the X-Z plane and taken along line 3-3 (shown in FIG. 2). One trapezoidal mounting rail 210 for each of mounting rail arrays 212, 214, 216, 218, and 220 is shown with arrays 212 through 220 extending into the sheet along y-axis 158 (shown in FIGS. 1 and 2). In the exemplary, each mounting rail 210 includes four apexes 240, 242, 244, and 246. Apex 240 is opposite apex 244 and apex 242 is opposite apex 246. Mounting rails 210 have different configurations depending upon their position within supermirror assembly 200.

FIG. 4 is a schematic view of a first exemplary mounting rail 250 that may be used with supermirror assembly 200 (shown in FIG. 3). Referring to FIGS. 3 and 4, first mounting rail 250 is positioned within mounting rail array 212. First mounting rail 250 includes a mounting groove 252 formed within apex 240. Mounting groove 252 is configured to receive first edge 232 of mirrored segment 222 and maintain mirrored segment 222 in position through a friction fit. Alternatively, any coupling mechanism that enables operation of supermirror assembly 200 as described herein is used, including, without limitation, mounting shims and adhesives.

FIG. 5 is a schematic view of a second mounting rail 260 that may be used with supermirror assembly 200 (shown in FIG. 3). Referring to FIGS. 3 and 5, second mounting rail 260 is positioned within mounting rail arrays 214, 216, and 218. Second mounting rail 260 includes a first mounting groove 262 and a second mounting groove 264 formed within apexes 244 and 240, respectively. First mounting groove 262 is configured to receive second edge 234 of mirrored segments 222, 224, and 226 and maintain mirrored segments 222, 224, and 226 in position through a friction fit. Second mounting groove 264 is configured to receive first edge 232 of mirrored segments 224, 226, and 228 and maintain mirrored segments 224, 226, and 228 in position through a friction fit. Alternatively, any coupling mechanism that enables operation of supermirror assembly 200 as described herein is used, including, without limitation, mounting shims and adhesives.

FIG. 6 is a schematic view of a third exemplary mounting rail 270 that may be used with supermirror assembly 200 (shown in FIG. 3). Referring to FIGS. 3 and 6, third mounting rail 270 is positioned within mounting rail array 220. Third mounting rail 270 includes a mounting groove 272 formed within apex 244. Mounting groove 272 is configured to receive second edge 234 of mirrored segment 228 and maintain mirrored segment 228 in position through a friction fit. Alternatively, any coupling mechanism that enables operation of supermirror assembly 200 as described herein is used, including, without limitation, mounting shims and adhesives.

Referring to FIG. 3, mounting grooves 252 are aligned within mounting rail array 212 to receive first edge 232 of mirrored segment 222 and mounting grooves 262 are aligned within mounting rail array 214 to receive second edge 234 of mirrored segment 222. During installation, mirrored segment 222 is slid into position through mounting grooves 252 and mounting grooves 262.

Similarly, mounting grooves 264 are aligned within mounting rail array 214 to receive first edge 232 of mirrored segment 224 and mounting grooves 262 are aligned within mounting rail array 216 to receive second edge 234 of mirrored segment 224. During installation, mirrored segment 224 is slid into position through mounting grooves 262 and mounting grooves 264.

Also, similarly, mounting grooves 264 are aligned within mounting rail array 216 to receive first edge 232 of mirrored segment 226 and mounting grooves 262 are aligned within mounting rail array 218 to receive second edge 234 of mirrored segment 226. During installation, mirrored segment 226 is slid into position through mounting grooves 262 and mounting grooves 264.

Further, similarly, mounting grooves 264 are aligned within mounting rail array 218 to receive first edge 232 of mirrored segment 228 and mounting grooves 272 are aligned within mounting rail array 220 to receive second edge 234 of mirrored segment 228. During installation, mirrored segment 228 is slid into position through mounting grooves 262 and mounting grooves 264.

In the exemplary embodiment, each mirrored segment 222 through 228 includes a reflective surface 280 at least partially oriented toward MFXS 112 and x-axis 152. Also, in the exemplary embodiment, the general shape of mirrored segments 222 through 228 is complimentary to a parabola 282 defined within the X-Z plane with an origin at MFXS 112. Supermirror assembly 200 is symmetrical about x-axis 152. Therefore, only half of supermirror assembly 200 is shown in FIG. 3. Also, in general, a curvature of mirrored segments 222 through 228 is reduced such that segments 222 through 228 are substantially linear with a substantially constant slope with respect to x-axis 152. A small amount of curvature is tolerated in mirrored segment 222. Alternatively, substantially no curvature is tolerated within any mirrored segment.

In operation, MFXS 112 radiates x-ray pencil beams 134 that form fan beam 150 (both shown in FIG. 1) from each focus point of MFXS 112 such that fan beam 150 fans out in the X-Y plane and the X-Z plane. In the X-Z plane, at least a portion of the fanning x-rays 134 emitted from MFXS 112 intersect mirrored surfaces 280 and are reflected into a parallel x-ray beam (not shown) at a coherent reflection angle, thereby increasing the x-ray flux in XDI system 100.

Figure 7:
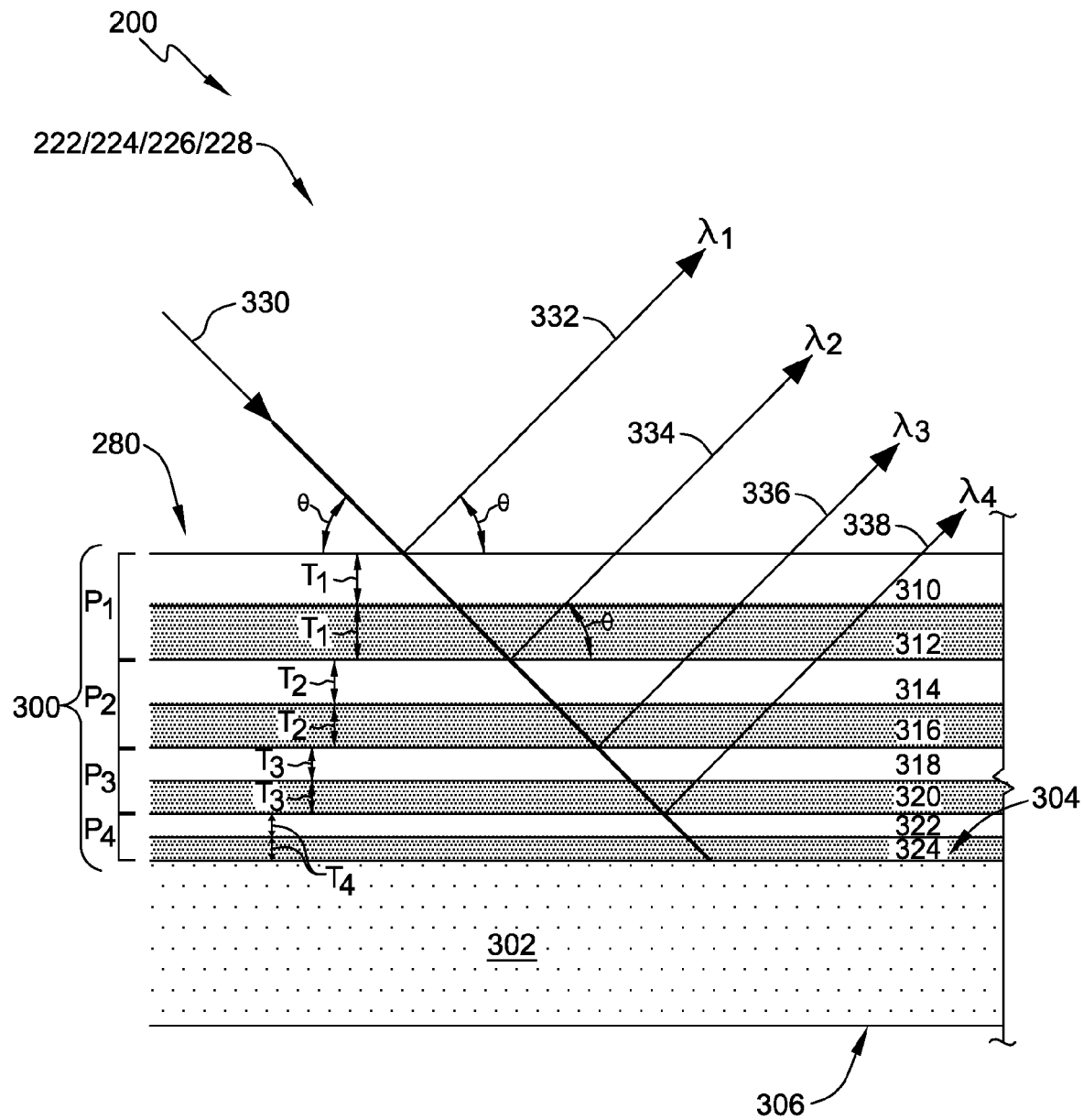

FIG. 7 is a schematic cross-sectional view of one of supermirror segments 222, 224, 226, and 228 that may be used with supermirror assembly 200. In the exemplary embodiment, supermirror segments 222, 224, 226, and 228 each include reflective surface 280 that includes a plurality of depth-graded layers 300 formed on top of a substrate 302. Substrate 302 is a glass sheet with a coated side 304 and an uncoated side 306. Also, in the exemplary embodiment, substrate 302 is about 0.3 mm thick. Alternatively, substrate 302 has any thickness that enables operation of supermirror assembly 200 as described herein.

Depth-graded layers 300 include multiple layers of high- and low-density materials, such as tungsten and silicon. Specifically, depth-graded layers 300 includes a first pair $P_1$ of layers including a first low-density silicon layer 310 and a first high-density tungsten layer 312. Similarly, depth-graded layers 300 includes a second pair $P_2$ of layers including a second low-density silicon layer 314 and a second high-density tungsten layer 316. Also, similarly, depth-graded layers 300 includes a third pair $P_3$ of layers including a third low-density silicon layer 318 and a third high-density tungsten layer 320. Further, similarly, depth-graded layers 300 includes a fourth pair $P_4$ of layers including a fourth low-density silicon layer 322 and a fourth high-density tungsten layer 324. In the exemplary embodiment, a thickness $T_1$ for each of layers 310 and 312, a thickness $T_2$ for each of layers 314 and 316, a thickness $T_3$ for each of layers 318 and 320, and a thickness $T_4$ for each of layers 320 and 324 is in the order of magnitude of nanometers. In the exemplary embodiment, thicknesses $T_1$ through $T_4$ are within a range between approximately 2 nanometers and approximately 20 nanometers. Alternatively, depth-graded layers 300 includes any number of pairs of alternating layers having any thicknesses that enable operation of supermirror assembly 200 as described herein.

An x-ray beam 330 is transmitted to super mirror assembly 300 from MFXS 112 (shown in FIGS. 1-3). Beam 330 includes photons having a variety of wavelengths ($\lambda$), i.e., x-ray beam 300 is polychromatic. As polychromatic beam 330 intersects first low-density silicon layer 310 at an angle $\theta$, a substantially monochromatic beam 332 is reflected at a first wavelength $\lambda_1$ at approximately angle $\theta$. Similarly, at the remainder of silicon-tungsten interfaces, substantially monochromatic beams 334, 336, and 338 are reflected at approximately angle $\theta$ with second, third, and fourth wavelengths $\lambda_2$, $\lambda_3$, and $\lambda_4$, respectively. The remainder of beam 330 is either transmitted through substrate 302 or absorbed. As such, the strength of an x-ray beam including beams 332 through 338 is much greater than beams reflected through a simple mirror.

The above described multi-detector inverse fan beam (MIFB) x-ray diffraction imaging (XDI) systems facilitate a cost-effective integration of a supermirror within the MIFB XDI system. The supermirrors described herein reflect x-rays to reduce the number of x-rays lost due to standard divergent flux spreading, i.e., x-ray fanning. Specifically, the supermirrors described herein facilitate integration of x-ray supermirrors in an XDI primary collimator to enhance x-ray flux while reducing power draws. Also, the supermirrors described herein include mounting rails that facilitate mounting the supermirrors in the XDI systems to be compatible with conventional MIFB XDI topologies with an "edge-on" mirror-edge-in-rail-slot configuration rather than the known "face-on" framing configuration. As such, the supermirrors described herein facilitate multiple planes of x-ray fan beams from a single array of point x-ray sources. In addition, since the mounting rails are positioned in regions that have little x-ray flux values, there is substantially no loss of x-ray radiation through supermirror frame holders that would otherwise obscure useful x-rays. Furthermore, the mirror support rails are manufactured from strong, but lightweight and inexpensive materials, thereby decreasing the weight and cost of the MIFB XDI systems described herein.

A technical effect of the systems and methods described herein includes at least one of: (a) increasing the integrability of x-ray supermirrors in an XDI primary collimator to enhance photon flux while reducing wall power requirements; (b) facilitating a compatibility of supermirror support mechanisms with conventional MIFB XDI topologies; (c) facilitating adapting a plurality of multiple fan beam XDI configurations through edge-on, rather than face-on, fixture of the supermirrors; (d) decreasing a loss of x-ray radiation through the otherwise obscuring supermirror frame holders; (e) facilitating the ruggedness of the supermirrors through the use of strong materials for the associated mirror mounting rails; and (f) facilitating an increase in retained x-ray radiation through precise and accurate placement of the supermirrors in the mounting rails.

Exemplary embodiments of multi-detector inverse fan beam (MIFB) x-ray diffraction imaging (XDI) systems are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other XDI security screening system applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An x-ray diffraction imaging (XDI) system comprising:
a plurality of x-ray sources configured to generate x-rays directed toward an object;
a primary collimator positioned a distance from said plurality of x-ray sources, wherein a plurality of nodes are defined within said primary collimator at a plurality of node distances from said plurality of x-ray sources, wherein each node of said plurality of nodes defines an x-ray intersection region; and
a supermirror assembly comprising a plurality of mounting rails positioned adjacent said plurality of nodes.

2. The XDI system in accordance with claim 1, wherein said XDI system further comprises a plurality of detectors, wherein said plurality of x-ray sources, said primary collimator, and said plurality of detectors define a first axis extending therethrough, said plurality of x-ray sources define a second axis extending therethrough, the first axis perpendicular to the second axis, the first axis and the second axis define an x-ray fan plane, wherein each node distance of the plurality of node distances is defined by:

$$X(N)=L/[1+(N*P_t)/P_s],$$

where $X(N)$ is the node distance, N is an integer, L is a length between said plurality of x-ray sources and said plurality of detectors along the first axis, $P_t$ is a detector pitch between each detector of said plurality of detectors, and $P_s$ is a source pitch between each x-ray source of said plurality of x-ray sources.

3. The XDI system in accordance with claim 2, wherein N includes a plurality of integers starting at 1, wherein said primary collimator defines a plurality of node arrays therein, wherein the number of said plurality of node arrays is equal to a value of the largest integer defined within N.

4. The XDI system in accordance with claim 2, wherein said plurality of node arrays are substantially parallel to each other and substantially parallel to the x-ray fan plane.

5. The XDI system in accordance with claim 2, wherein said plurality of mounting rails extend a length perpendicular to the x-ray fan plane.

6. The XDI system in accordance with claim 1, wherein said supermirror assembly further comprises at least one mirrored segment configured to be received by said plurality of mounting rails.

7. The XDI system in accordance with claim 6, wherein said at least one mirrored segment comprises a first edge and a second edge opposite said first edge.

8. The XDI system in accordance with claim 7, wherein said plurality of mounting rails comprises a first mounting rail configured to receive said first edge and a second mounting rail configured to receive said second edge.

9. The XDI system in accordance with claim 7, wherein said plurality of mounting rails are substantially trapezoidal.

10. The XDI system in accordance with claim 9, wherein each mounting rail of said plurality of mounting rails defines a first apex and a second apex opposite said first apex, at least one of said first apex and said second apex comprise at least one mounting groove defined therein, said at least one mounting groove configured to receive one of said first edge and said second edge.

11. The XDI system in accordance with claim 6, wherein said at least one mirrored segment comprises a plurality of mirrored segments, wherein at least a portion of said plurality of mirrored segments comprises a reflective surface that is substantially linear.

12. The XDI system in accordance with claim 1, wherein said XDI system is a multiple inverse fan beam (MIFB) XDI system.

13. A supermirror assembly for an x-ray diffraction imaging (XDI) system, the XDI system including a plurality of x-ray sources and a primary collimator positioned a distance from the plurality of x-ray sources, wherein a plurality of nodes are defined within the primary collimator at a plurality of node distances from the plurality of x-ray sources, wherein each node of the plurality of nodes defines an x-ray intersection region, said supermirror assembly comprising a plurality of mounting rails positioned adjacent the plurality of nodes.

14. The supermirror assembly in accordance with claim 13, wherein the XDI system further includes a plurality of detectors, wherein the plurality of x-ray sources, the primary collimator, and the plurality of detectors define a first axis extending therethrough, the plurality of x-ray sources define a second axis extending therethrough, the first axis perpendicular to the second axis, the first axis and the second axis define an x-ray fan plane, wherein said plurality of mounting rails extend a length perpendicular to the x-ray fan plane.

15. The supermirror assembly in accordance with claim 13 further comprising at least one mirrored segment configured to be received by said plurality of mounting rails.

16. The supermirror assembly in accordance with claim 15, wherein said at least one mirrored segment comprises a first edge and a second edge opposite said first edge.

17. The supermirror assembly in accordance with claim 16, wherein said plurality of mounting rails comprises a first mounting rail configured to receive said first edge and a second mounting rail configured to receive said second edge.

18. The supermirror assembly in accordance with claim 16, wherein said plurality of mounting rails are substantially trapezoidal.

19. The supermirror assembly in accordance with claim 18, wherein each mounting rail of said plurality of mounting rails defines a first apex and a second apex opposite said first apex, at least one of said first apex and said second apex comprise at least one mounting groove defined therein, said at least one mounting groove configured to receive one of said first edge and said second edge.

20. The supermirror assembly in accordance with claim 15, wherein said at least one mirrored segment comprises a plurality of mirrored segments, wherein at least a portion of said plurality of mirrored segments comprises a reflective surface that is substantially linear.

\* \* \* \* \*